(12) United States Patent
Tsukernik

(10) Patent No.: US 6,494,861 B1
(45) Date of Patent: *Dec. 17, 2002

(54) DRUG DELIVERY SYSTEM

(75) Inventor: Vladimir Tsukernik, West Roxbury, MA (US)

(73) Assignee: Boston Scientific Corporation, Natick, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/783,268

(22) Filed: Jan. 15, 1997

(51) Int. Cl.$^7$ .............................................. A61M 1/00
(52) U.S. Cl. ...................................................... 604/67
(58) Field of Search ............................... 604/96, 97, 98, 604/99, 100, 102, 30, 31, 53, 65–67, 104, 118; 606/191, 192, 193, 194; 128/DIG. 12, DIG. 13

(56) References Cited

U.S. PATENT DOCUMENTS

| | | | |
|---|---|---|---|
| 3,699,956 A | 10/1972 | Kitrilakis et al. ............ | 128/348 |
| 4,026,296 A | 5/1977 | Stoy et al. .............. | 128/349 B |
| 4,299,226 A | 11/1981 | Banka | |
| 4,330,497 A | 5/1982 | Agdanowski ............... | 264/173 |
| 4,364,392 A | 12/1982 | Strother et al. ............. | 128/325 |
| 4,417,576 A | 11/1983 | Baran ..................... | 128/207.15 |
| 4,423,725 A | 1/1984 | Baran et al. ........... | 128/207.15 |
| 4,448,195 A | 5/1984 | LeVeen et al. .............. | 128/344 |
| 4,481,323 A | 11/1984 | Sterling | |
| 4,515,593 A | 5/1985 | Norton ........................ | 604/265 |
| 4,589,873 A | 5/1986 | Schwartz et al. ........... | 604/265 |
| 4,592,340 A | 6/1986 | Boyles ........................... | 128/1 |
| 4,603,152 A | 7/1986 | Laurin et al. ............... | 604/265 |
| 4,636,195 A | 1/1987 | Wolinsky | |
| 4,693,243 A | 9/1987 | Buras .................... | 128/207.15 |

(List continued on next page.)

FOREIGN PATENT DOCUMENTS

| | | |
|---|---|---|
| DE | 1196327 | 7/1965 |
| DE | A 380205 | 1/1994 |
| EP | 0 166 998 B1 | 1/1986 |
| EP | 0 372 088 A1 | 6/1990 |

(List continued on next page.)

OTHER PUBLICATIONS

Chapman et al., "A Bioabsorbable Stent: Initial Experimental Results", *Circulation* (Supp III) 82:0283 (abstract) (Oct. 1990).

(List continued on next page.)

*Primary Examiner*—Michael Buiz
*Assistant Examiner*—Manuel Mendez
(74) *Attorney, Agent, or Firm*—Fish & Richardson P.C.

(57) ABSTRACT

A system for controlling delivery of a physiological fluid internally to a patient from a balloon catheter. The system includes a controller, an inflation-fluid pressurizer for maintaining inflation fluid in an inflation-fluid conduit under pressure, and a physiological-fluid pressurizer for maintaining physiological fluid in a physiological-fluid conduit under pressure. The inflation-fluid pressurizer is connected to receive signals from the controller to cycle pressure in the inflation-fluid conduit between a balloon inflating pressure and a balloon deflating pressure. The physiological-fluid pressurizer is connected to receive signals from the controller to cycle pressure in the physiological-fluid conduit between a fluid delivery pressure and a resting pressure. The controller is programmed to synchronize signals to the inflation-fluid pressurizer with signals to the physiological-fluid pressurizer. Thus, periods of balloon inflating pressure in the inflation-fluid conduit generally overlap with periods of fluid delivery pressure in the physiological-fluid conduit, and periods of balloon deflating pressure in the inflation-fluid conduit generally overlap with periods of resting pressure in the physiological-fluid conduit.

13 Claims, 1 Drawing Sheet

U.S. PATENT DOCUMENTS

| | | | |
|---|---|---|---|
| 4,714,460 A | 12/1987 | Calderon | |
| 4,732,930 A | 3/1988 | Tanaka et al. | |
| 4,769,013 A | 9/1988 | Lorenz et al. | 604/265 |
| 4,784,647 A | 11/1988 | Gross | 604/178 |
| 4,820,270 A | 4/1989 | Hardcastle et al. | 604/96 |
| 4,832,688 A | 5/1989 | Sagae et al. | 604/101 |
| 4,876,126 A | 10/1989 | Takemura et al. | 428/35.7 |
| 4,909,258 A | 3/1990 | Kuntz et al. | 128/658 |
| 4,923,450 A | 5/1990 | Maeda et al. | 604/265 |
| 4,950,256 A | 8/1990 | Luther et al. | 604/265 |
| 4,983,166 A | 1/1991 | Yamawaki | 604/96 |
| 4,993,412 A | 2/1991 | Murphy-Chutorian | 606/7 |
| 4,994,033 A | 2/1991 | Shockey et al. | 604/101 |
| 5,021,044 A | 6/1991 | Sharkawy | 604/53 |
| 5,026,607 A | 6/1991 | Kiezulas | 428/423.7 |
| 5,041,100 A | 8/1991 | Rowland et al. | 604/265 |
| 5,047,045 A | 9/1991 | Arney et al. | 604/194 |
| 5,049,132 A | 9/1991 | Shaffer et al. | 604/101 |
| 5,087,244 A | 2/1992 | Wolinsky | |
| 5,091,205 A | 2/1992 | Fan | 604/265 |
| 5,102,402 A | 4/1992 | Dror et al. | 604/265 |
| 5,120,322 A | 6/1992 | Davis et al. | 604/265 |
| 5,135,516 A | 8/1992 | Sahatjian et al. | 604/265 |
| 5,163,906 A | 11/1992 | Ahmadi | 604/101 |
| 5,176,646 A | 1/1993 | Kuroda | |
| 5,180,366 A | 1/1993 | Woods | 604/96 |
| 5,213,576 A | 5/1993 | Abiuso et al. | 604/96 |
| 5,213,580 A | 5/1993 | Slepian et al. | 623/1 |
| 5,232,444 A | 8/1993 | Just et al. | 604/96 |
| 5,254,089 A | 10/1993 | Wang | |
| 5,304,120 A | 4/1994 | Crandell et al. | 604/53 |
| 5,304,121 A | 4/1994 | Sahatjian | 604/53 |
| 5,328,470 A | 7/1994 | Nabel et al. | |
| 5,330,467 A | 7/1994 | Abela | |
| 5,336,178 A | 8/1994 | Kaplan et al. | |
| 5,336,615 A | 8/1994 | Bell et al. | |
| 5,370,614 A | 12/1994 | Amundson et al. | |
| 5,439,446 A | 8/1995 | Barry | |
| 5,462,752 A | 10/1995 | Chao | |
| 5,553,508 A | 9/1996 | Dabberdt et al. | |
| 5,575,815 A | 11/1996 | Slepian | |
| 5,674,192 A | 10/1997 | Sahatjian et al. | |

FOREIGN PATENT DOCUMENTS

| | | |
|---|---|---|
| EP | 0 379 156 A2 | 7/1990 |
| EP | 0 399 712 A1 | 11/1990 |
| EP | 0 441 516 A2 | 8/1991 |
| GB | 2112646 | 7/1983 |
| JP | 53006430 | 1/1978 |
| JP | 54-35036 | 10/1979 |
| SU | 1069826 | 1/1984 |
| WO | WO 89/12478 | 12/1989 |
| WO | WO 91/05816 | 5/1991 |
| WO | WO 91/08790 | 6/1991 |
| WO | WO 92/11895 | 7/1992 |
| WO | WO 92/11896 | 7/1992 |
| WO | WO 92/13566 | 8/1992 |
| WO | WO 92/15282 | 9/1992 |
| WO | WO 93/11751 | 6/1993 |
| WO | WO 96/11940 | 4/1996 |

OTHER PUBLICATIONS

Deutsch et al., "Low Stress Angioplasty at 60° C.; Attenuated Arterial Barotrauma", Circulation (Supp. III) 82:0281 (abstract) (Oct. 1990).

Guyton et al., "Inhibition of Rat Arterial Smooth Muscle Cell Proliferation by Heparin: In Vivo Studies with Anticoagulant and Nonanticoagulant Heparin," *Cir. Res.* 46:625–634 (May 1980).

Ilmain et al., "Volume Transition in a Gel Driven by Hydrogen Bonding", 1991, *Nature*, 349:400–401.

Irie et al. "Stimuli–responsive polymers: chemical induced reversible phase separation of an aqueous soution of poly(N–isopropylacrylamide) with pendent crown ether groups", 1993, *Polymer*, 34(21):4531–35.

Langer, "Drug Delivery," *IUPAC* Meeting, Montreal, Canada, (Jul. 12, 1990).

Mamada et al., "Photoinduced Phase Transition of Gels", 1990, *Macromolecules*, 23:1517–19.

McMath et al., "Experimental Application of Bioprotective Materials to Injured Arterial Surfaces with Laser Balloon Angioplasty", *Circulation* (Supp. III) 82:0282 (abstract) (Oct. 1990).

Suzuki et al., "Phase Transition in Polymer Gels Induced by Visible Light", 1990, *Nature*, 346:345–47.

Tarcha, "Diffusion Controlled Systems: Hydrogels", *Polymers for Controlled Drug Delivery*, CRC Press, Inc., 1991, Ch. 2, pp. 16–37.

Thompson et al., "Heparin and Growth Control of Vascular Cells," *Ann. N.Y. Acad. Sci.* 556:255–267 (1989).

Tidd et al., "Comparison of Hydrophilic Polymer–Coated Latex, uncoated Latex and PVC Indwelling Balloon Catheters in the Prevention of Urinary Infection," *J.Urol.* 48:285–291 (1976).

Tokuhiro et al., "NMR Study of Poly(N–isopropylaacrylamide) Gels near Phase Transition", 1991, *Macromolecules*, 24:2936–43.

Waller B.F. et al., "Vessel Wall Pathology After Angioplasty", Cardio, Aug. 1990, p. 57, 70–72, 81.

Waller et al., "Morphologic Observations Late after Coronary Balloon Angioplasty" Mechanisms of Acute Injury and Relationship to Restenosis, *Radio.* 174:961–967 (Mar. 1990).

Wolinsky H. et al., "Local Introduction of Drugs into the Arterial Wall: A Percutaneous Catheter Technique", Journal of Interventional Cardiology, vol. 2, No. 4, 1989, pp. 219–228.

The Andreas Gruentzig Cardiovascular Center News Letter (Spring 1990).

Supplementary European Search Report, EP 92 90 3283, mailed Sep. 15, 1993.

International Search Report for PCT/US91/09804, mailed Apr. 8, 1992.

International Search Report, PCT/US91/09805, mailed Apr. 8, 1992.

International Search Report, PCT/US94/08394, mailed Dec. 23, 1994.

Slepian, "Polymeric Endoluminal Gel Paving: Therapeutic Hydrogel Barriers and Sustained Drug Delivery Depots for Local Arterial Wall Biomanipulation", *Semin Intervent Cardiol*, 1:103–116 (1996).

Szikora et al., "Endovascular Treatment of Experimental Aneurysms with Lipid Polymers: The Protective Potential of Stents", *Neurosurgery*, 38(2):339–47 (1996).

Wakhloo et al., "Self–Expanding and Balloon–Expandable Stents in the Treatment of Carotid Aneurysms: An Experimental Study in a Canine Model", Am. J. *Neuroradiology*, 15:494–502 (1994).

DRUG DELIVERY SYSTEM

BACKGROUND OF THE INVENTION

This application relates to a system for controlling delivery of a physiological fluid internally to a patient from a balloon catheter.

Balloon catheters may be used to deliver drugs to tissue at a desired location of a patient's body, such as a blood vessel. Typically, the balloon catheter is positioned at the desired location for drug delivery from one or more distal drug delivery outlets, e.g., on the surface of the balloon or on the catheter shaft. The balloon is inflated through a balloon inflation conduit to block the flow of blood in the vessel, thereby enhancing local drug delivery. A stepper motor may be connected to an infusion syringe containing the drug to provide a continuous flow of drug during the procedure.

SUMMARY OF THE INVENTION

One aspect of the invention generally features a system for controlling delivery of a physiological fluid internally to a patient from a balloon catheter. The balloon catheter includes a distal balloon connected to a catheter shaft, an inflation-fluid conduit connecting the balloon to a proximal source of pressurized balloon inflation fluid, and a physiological-fluid conduit connecting a fluid-delivery outlet of the balloon catheter to a proximal source of pressurized physiological fluid.

The system includes a controller, an inflation-fluid pressurizer for maintaining inflation fluid in the inflation-fluid conduit under pressure, and a physiological-fluid pressurizer for maintaining physiological fluid in the physiological-fluid conduit under pressure. The inflation-fluid pressurizer is connected to receive signals from the controller to cycle pressure in the inflation-fluid conduit between a balloon inflating pressure and a balloon deflating pressure. The physiological-fluid pressurizer is connected to receive signals from the controller to cycle pressure in the physiological-fluid conduit between a fluid delivery pressure and a resting pressure.

The controller is programmed to synchronize signals to the inflation-fluid pressurizer with signals to the physiological-fluid pressurizer. Thus, periods of balloon inflating pressure in the inflation-fluid conduit generally overlap with periods of fluid delivery pressure in the physiological-fluid conduit, and periods of balloon deflating pressure in the inflation-fluid conduit generally overlap with periods of resting pressure in the physiological-fluid conduit.

In preferred embodiments, the system also includes a holder sized and shaped to hold both an inflation fluid delivery chamber having a first moveable wall and a physiological fluid delivery chamber having a second moveable wall. Movement of the first moveable wall changes the volume of the inflation fluid delivery chamber, and movement of the second moveable wall changes the volume of the physiological fluid delivery chamber.

The inflation-fluid pressurizer may have a first driver and a first connector sized and shaped for connection of the first driver to a first movable wall of an inflation fluid delivery chamber. The physiological-fluid pressurizer may have a second driver and a second connector sized and shaped for connection of the second driver to a second movable wall of a physiological fluid delivery chamber. The first driver may be connected to the controller via a first circuit, and the second driver is connected to the controller via a second circuit.

The first connector may be a push-pull coupling, so that the first driver can push the first moveable wall to decrease the volume of the inflation fluid delivery chamber and pull the first moveable wall to increase the volume of the inflation fluid delivery chamber. The second connector may be a push-only coupling, so that the second driver can push the second moveable wall to decrease the volume of the physiological fluid delivery chamber. The second driver cannot pull the second moveable wall to increase the volume of the physiological fluid delivery chamber, thus reducing the opportunity for undesired retrograde movement of bodily fluids into the physiological-fluid conduit.

The holder accommodates a first syringe with a plunger that moves the first movable wall. The push-pull coupling may include a flattened region of the plunger at least partially enveloped by a mating structure of the first driver. The movement of the first driver toward the inflation fluid delivery chamber thus pushes the plunger and moves the first moveable wall to decrease the volume of the inflation fluid delivery chamber, thereby increasing the pressure in the inflation-fluid conduit. The movement of the first driver away from the inflation fluid delivery chamber engages the plunger and moves the first moveable wall to increase the volume of the inflation fluid delivery chamber.

The holder may also accommodate a second syringe with a plunger that moves the second movable wall. The push-only coupling includes a flattened region of the plunger which mates with a flattened member of the second driver. The movement of the second driver toward the physiological fluid delivery chamber pushes the plunger and moves the second moveable wall to decrease the volume of the physiological fluid delivery chamber, thereby increasing the pressure in the physiological fluid delivery chamber. The movement of the second driver away from the physiological fluid delivery chamber disengages the flattened region of the plunger from the flattened structure of the second driver without changing the volume of the physiological fluid delivery chamber.

The first driver may include a first pneumatic cylinder that is independently controlled by a first solenoid relay. The first solenoid relay may be controlled by the controller. The second driver may include a second pneumatic cylinder that is independently controlled by a second solenoid relay. The second solenoid relay may be controlled by the controller, which includes a timer. The system may also include a housing that surrounds the holder.

Another aspect of the invention generally features a method for delivering a physiological fluid internally to a patient from a balloon catheter. The balloon catheter includes a distal balloon connected to a catheter shaft, an inflation-fluid conduit connecting the balloon to a proximal source of pressurized balloon inflation fluid, and a physiological-fluid conduit connecting a fluid-delivery outlet of the balloon catheter to a proximal source of pressurized physiological fluid.

The method uses a system comprising a controller, an inflation-fluid pressurizer for maintaining inflation fluid in the inflation-fluid conduit under pressure, and a physiological-fluid pressurizer for maintaining physiological fluid in the physiological-fluid conduit under pressure. The balloon is positioned at the internal location, and alternately inflated and deflated by cycling pressure in the inflation-fluid conduit between a balloon inflating pressure and a balloon deflating pressure. Physiological fluid is delivered to the internal location by cycling pressure in the physiological-fluid conduit between a fluid delivery pressure and a resting pressure. Pressure cycles in the inflation-fluid conduit are synchronized with pressure cycles in the physiological-fluid conduit. Thus, periods of balloon inflating pressure in the inflation-fluid conduit generally overlap with periods of fluid delivery pressure in the physiological-fluid conduit, and periods of balloon deflating pressure in the inflation-fluid conduit generally overlap with periods of resting pressure in the physiological-fluid conduit.

The physiological fluid may be a drug, such as thrombin, hirudin, hirulog, urokinase, low molecular weight heparin or other modified heparins, TPA, PPACK, 7E3, or any other antiplatelet, antiproliferative or antioxidant drug. The physiological fluid also may be any drug used in chemotherapy or any gene or gene construct used in gene therapy. The invention may be used to deliver drugs to locations in the vasculature, such as blood vessels or the heart. The invention also may be used to deliver drugs to body lumens, such as the alimentary tract, the reproductive system, the urinary tract or the biliary tree.

The invention increases the efficiency of irrigation of the tissue with the drug and, in some cases, may reduce the amount of time the flow of bodily fluid is interrupted. The invention also helps to eliminate the need for manual control of the balloon inflation and drug infusion so that the doctor may be free to monitor the procedure.

Other features and advantages will be apparent from the following drawings, description of the preferred embodiments and claims.

DESCRIPTION OF THE PREFERRED EMBODIMENTS

Figure 1:
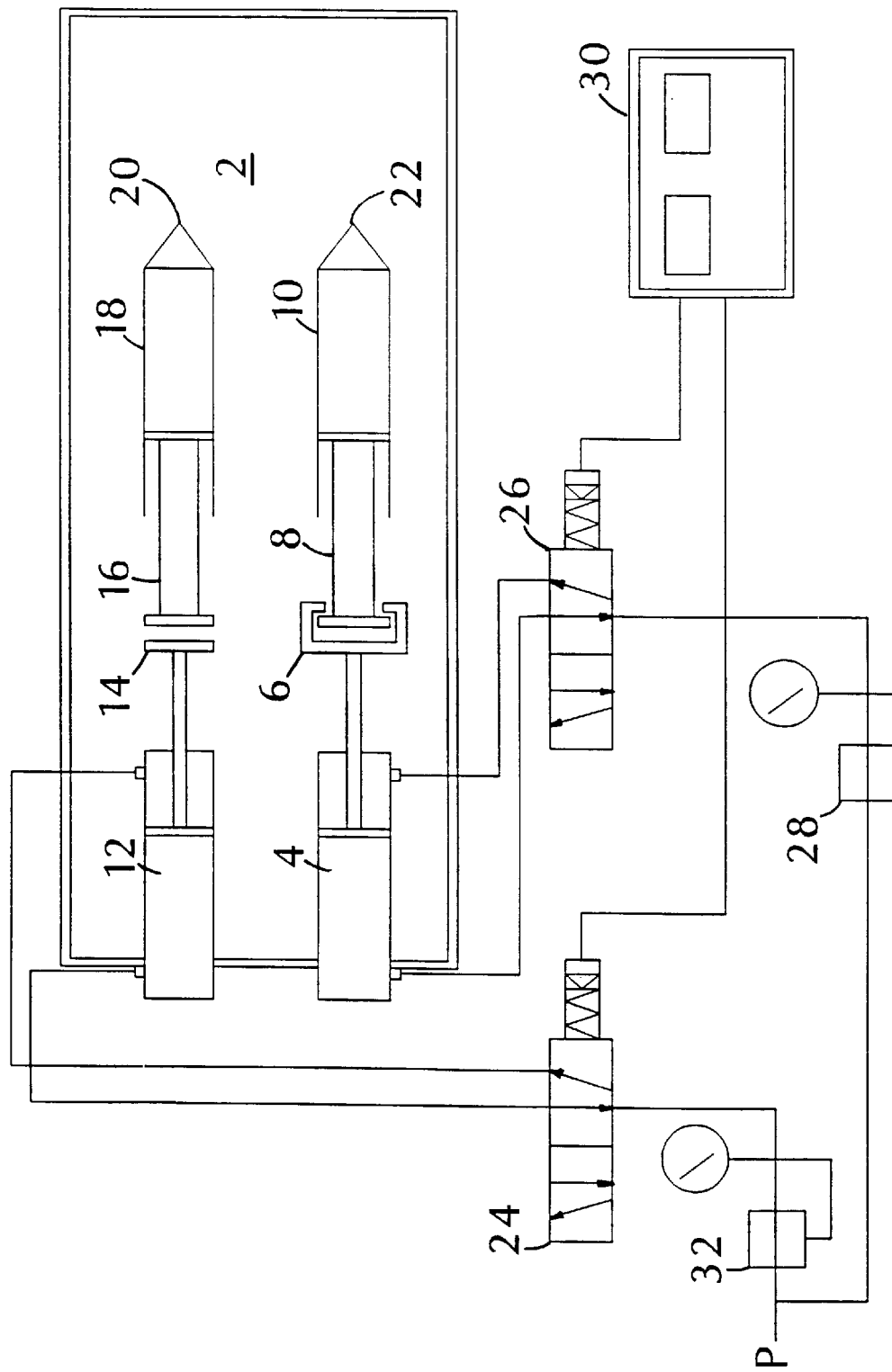
FIG. 1 is a diagram of a drug delivery system.

FIG. 1 shows a drug delivery system for controlling delivery of a drug internally to a patient from a balloon catheter (not shown). Typically, the balloon catheter includes a distal balloon connected to a catheter shaft, a lumen connecting the balloon to a proximal source of pressurized balloon inflation fluid, and a lumen connecting a drug delivery outlet of the balloon catheter to a proximal source of pressurized drug.

The system includes a housing 2 containing a pneumatic cylinder 4 having a push-pull coupling 6 for connecting with a plunger 8 of an inflation syringe 10 and a pneumatic cylinder 12 having a push-only coupling 14 for connecting with a plunger 16 of an infusion syringe 18. Inflation syringe 10 contains inflation fluid for inflating the balloon, and infusion syringe 18 contains the drug to be delivered to the tissue. Housing 2 has a holder, such as brackets or slots, for holding inflation syringe 10 and infusion syringe 18 securely in place. In this embodiment, the syringes are not included as part of the system.

Output ports 20, 22 of inflation syringe 10 and infusion syringe 18 are connected to the proximal end of the balloon catheter (not shown), so that the inflation syringe 10 is in fluid communication with the lumen connected to the balloon and the infusion syringe 18 is in fluid communication with the lumen connected to the drug delivery outlet.

The bent shape of coupling 6 of pneumatic cylinder 4 allows plunger 8 of inflation syringe 10 to be pushed forward and pulled backward by pneumatic cylinder 4. The pushing motion forces inflation fluid into the balloon and thus, inflates the balloon. The pulling motion deflates the balloon. The flat shape of coupling 14 of pneumatic cylinder 12 allows plunger 16 of infusion syringe 18 only to be pushed forward by pneumatic cylinder 12. This push-only motion prevents a vacuum from forming in the lumen connected to the drug delivery outlet.

Each pneumatic cylinder is connected to a two position/four way valve 24, 26. For example, valve 26 may be switched to port the pressure from a regulator to one side or the other of pneumatic cylinder 4 to cause plunger 8 to move either farther into inflation syringe 10 or move farther out of inflation syringe 10.

Valves 24, 26 are independently controlled by solenoid relays connected to programmable controller 30. Controller 30 is a microprocessor or a PC controller which is programmed to control the timing and duration of the balloon inflation and drug infusion, as described below. For example, because the inflated balloon blocks the flow of blood in the vessel, the balloon may be inflated for only a short period of time to avoid injury to the patient. Typically, in the vasculature, the balloon inflation time may range from approximately 30 seconds to two minutes. The preference is to keep the balloon inflation time as short as possible. Drug infusion is limited to two minutes or less, unless perfusion of the bodily fluid can be maintained during drug infusion, in which case the drug infusion may continue for 30 minutes or longer. In other locations, such as the urinary tract, the balloon may be inflated for 24 hours or more.

Valves 24, 26 are also connected to pressure regulators 28, 32 with gauges. The pressure applied to each pneumatic cylinder may be adjusted by the regulators to control the pressure applied to the syringes. Typically, in the vasculature, the balloon inflation pressure can range from approximately 5 to 18 atm. Drug infusion pressure is normally 5 atm or less, yielding flow rates from 0.5 to 25 ml/min. Drug infusion can be controlled by pressure or flow rate, but is typically controlled by pressure. The amount of pressure used to infuse the drug is important because too much pressure may damage the vessel wall, whereas too little pressure may not infuse the drug into the vessel wall but may allow it to be washed away by the bodily fluid. Balloon deflation is achieved by setting the inflation fluid to a pressure below the surrounding pressure at the treatment location. Typically during balloon angioplasty, a vacuum is created in the syringe attached to the balloon inflation port to cause balloon deflation. The resting pressure for drug infusion may be set slightly above the pressure typical in the treatment location to avoid retrograde flow of bodily fluid into the lumen connected to the drug delivery outlet. Alternately, the resting pressure for drug infusion could be set high enough above the pressure typical in the treatment location to allow some drug infusion to continue during the period of resting pressure.

II. Use

Delivery of a drug internally to a patient from a balloon catheter may be controlled by the drug delivery system as follows. After the balloon catheter is positioned at the desired location for drug delivery, the system synchronizes the cycling of pressure for balloon inflation with the cycling of pressure for drug infusion. For example, the system may have the following sequence of operations for delivering a drug to a blood vessel.

A signal from controller 30 activates valve 26 of cylinder 4 to apply pressure through coupling 6 to plunger 8, thus applying pressure to inflation fluid and inflating the balloon. When the desired balloon inflation pressure has been achieved, so that the balloon has effectively stopped blood circulation in the vessel, controller 30 begins the drug delivery cycle by sending a signal to valve 24 of cylinder 12 to apply pressure through coupling 14, thereby pushing plunger 16 of infusion syringe 18 forward and forcing the drug to flow out of the drug delivery outlet at the treatment location. Typically, the controller will be programmed to deliver a pre-set volume of drug for each cycle. Once the drug has been delivered, inflation pressure is released so that coupling 6 pulls plunger 8 of inflation syringe 10 backward and draws the inflation fluid back into the syringe, thereby deflating the balloon. Simultaneously, infusion pressure is released so that the coupling 14 is no longer pushing plunger 16 of infusion syringe 18 forward. The system pauses for a few moments so that blood may flow in the blood vessel before repeating the cycle.

What is claimed is:

1. A system for controlling delivery of a physiological fluid internally to a patient from a balloon catheter, the balloon catheter comprising a distal balloon connected to a catheter shaft, an inflation-fluid conduit connecting the balloon to a proximal source of pressurized balloon inflation fluid, and a physiological-fluid conduit connecting a fluid-delivery outlet of the balloon catheter to a proximal source of pressurized physiological fluid; the system comprising (a) a controller;

(b) an inflation-fluid pressurizer for maintaining inflation fluid in the inflation-fluid conduit under pressure, the inflation-fluid pressurizer being connected to receive signals from the controller to cycle pressure in the inflation-fluid conduit between a balloon inflating pressure and a balloon deflating pressure;

(c) a physiological-fluid pressurizer for maintaining physiological fluid in the physiological-fluid conduit under pressure, the physiological-fluid pressurizer being connected to receive signals from the controller to cycle pressure in the physiological-fluid conduit between a fluid delivery pressure and a resting pressure;

the controller being programmed to synchronize the signals to the inflation-fluid pressurizer with the signals to the physiological-fluid pressurizer, such that periods of balloon inflating pressure in the inflation-fluid conduit generally overlap with periods of fluid delivery pressure in the physiological-fluid conduit, and periods of balloon deflating pressure in the inflation-fluid conduit generally overlap with periods of resting pressure in the physiological-fluid conduit.

2. The system of claim 1 further comprising a holder sized and shaped to hold both: (i) an inflation fluid delivery chamber having a first moveable wall, movement of the first moveable wall changing the volume of the inflation fluid delivery chamber, and (ii) a physiological fluid delivery chamber having a second moveable wall, movement of the second moveable wall changing the volume of the physiological fluid delivery chamber.

3. The system of claim 1 in which the inflation-fluid pressurizer comprises a first driver and a first connector sized and shaped for connection of the first driver to a first movable wall of an inflation fluid delivery chamber, movement of the first moveable wall changing the volume of the inflation fluid delivery chamber, and the physiological-fluid pressurizer comprises a second driver and a second connector sized and shaped for connecting of the second driver to a second movable wall of a physiological fluid delivery chamber, movement of the second moveable wall changing the volume of the physiological fluid delivery chamber, the first driver being connected to the controller via a first circuit, and the second driver being connected to the controller via a second circuit.

4. The system of claim 3 in which the first connector is a push-pull coupling, whereby the first driver can push the first moveable wall to decrease the volume of the inflation fluid delivery chamber and the first driver can pull the first moveable wall to increase the volume of the inflation fluid delivery chamber.

5. The system of claim 3 in which the second connector is a push-only coupling, whereby the second driver can push the second moveable wall to decrease the volume of the physiological fluid delivery chamber, and the second driver cannot pull the second moveable wall to increase the volume of the physiological fluid delivery chamber.

6. The system of claim 4 in which the holder accommodates a first syringe, the first syringe comprising a plunger which moves the first movable wall, and the push-pull coupling comprises a flattened region of the plunger at least partially enveloped by a mating structure of the first driver, whereby movement of the first driver toward the inflation fluid delivery chamber pushes the plunger and moves the first moveable wall to decrease the volume of the inflation fluid delivery chamber, thereby increasing the pressure in the inflation-fluid conduit, and movement of the first driver away from the inflation fluid delivery chamber engages the plunger and moves the first moveable wall to increase the volume of the inflation fluid delivery chamber.

7. The system of claim 5 or claim 6 in which the holder accommodates a second syringe, the second syringe comprising a plunger which moves the second movable wall, and the push-only coupling comprises a flattened region of the plunger which mates with a flattened member of the second driver, whereby movement of the first driver toward the physiological fluid delivery chamber pushes the plunger and moves the second moveable wall to decrease the volume of the physiological fluid delivery chamber, thereby increasing the pressure in the physiological fluid delivery chamber, and movement of the second driver away from the physiological fluid delivery chamber disengages the flattened region of the plunger from the flattened structure of the second driver without changing the volume of the physiological fluid delivery chamber.

8. The system of claim 3 in which the first driver comprises a first pneumatic cylinder which is independently controlled by a first solenoid relay, said first solenoid relay being controlled by the controller.

9. The system of claim 3 or claim 8 in which the second driver comprises a second pneumatic cylinder which is independently controlled by a second solenoid relay, said second solenoid relay being controlled by the controller.

10. The system of claim 1, wherein the physiological fluid is a drug.

11. The system of claim 1, wherein the programmable controller comprises a timer.

12. The system of claim 2 in which the system further comprises a housing that surrounds the holder.

13. A method for delivering a physiological fluid internally to a patient from a balloon catheter, the balloon catheter comprising a distal balloon connected to a catheter shaft, an inflation-fluid conduit connecting the balloon to a proximal source of pressurized balloon inflation fluid, and a physiological-fluid conduit connecting a fluid-delivery outlet of a balloon catheter to a proximal source of pressurized physiological fluid; the method comprising:

provide a system comprising (a) a controller; (b) an inflation-fluid pressurizer for maintaining inflation fluid in the inflation-fluid conduit under pressure; and (c) a physiological-fluid pressurizer for maintaining physiological fluid in the physiological-fluid conduit under pressure;

alternately inflating and deflating the balloon at the internal location by cycling pressure in the inflation-fluid conduit between a balloon inflating pressure and a balloon deflating pressure;

alternately delivering physiological fluid at the internal location by cycling pressure in the physiological-fluid conduit between a fluid delivery pressure and a resting pressure;

synchronizing cycling of the pressure in the inflation-fluid conduit with cycling of the pressure in the physiological-fluid conduit, so that periods of balloon inflating pressure in the inflation-fluid conduit generally overlap with periods of fluid delivery pressure in the physiological-fluid conduit, and periods of balloon deflating pressure in the inflation-fluid conduit generally overlap with periods of resting pressure in the physiological-fluid conduit.

* * * * *